(12) United States Patent
Luyken et al.

(10) Patent No.: US 7,501,047 B2
(45) Date of Patent: Mar. 10, 2009

(54) METHOD FOR PURIFYING CAPROLACTAM

(75) Inventors: Hermann Luyken, Ludwigshafen (DE); Andreas Ansmann, Wiesloch (DE); Christoph Benisch, Mannheim (DE); Peter Baβler, Viernheim (DE); Rolf-Hartmuth Fischer, Heidelberg (DE); Stefan Maixner, Schwetzingen (DE); Johann-Peter Melder, Böhl-Iggelheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 743 days.

(21) Appl. No.: 10/534,822

(22) PCT Filed: Nov. 11, 2003

(86) PCT No.: PCT/EP03/12558

§ 371 (c)(1),
(2), (4) Date: May 13, 2005

(87) PCT Pub. No.: WO2004/043915

PCT Pub. Date: May 27, 2004

(65) Prior Publication Data

US 2006/0090994 A1 May 4, 2006

(30) Foreign Application Priority Data

Nov. 13, 2002 (DE) ................................. 102 53 094

(51) Int. Cl.
*B01D 3/14* (2006.01)
*B01D 3/34* (2006.01)
*C07D 201/08* (2006.01)
*C07D 201/16* (2006.01)

(52) U.S. Cl. ............................. 203/35; 203/75; 203/77; 540/540

(58) Field of Classification Search ................... 203/2, 203/3, 14, 34, 35, 75, 77; 540/538, 539, 540/540
See application file for complete search history.

(56) References Cited

U.S. PATENT DOCUMENTS

| 496,941 A | 5/1893 | King |
| 4,026,854 A | 5/1977 | Buechner et al. |
| 4,720,328 A * | 1/1988 | Corbin et al. ................. 203/37 |

(Continued)

FOREIGN PATENT DOCUMENTS

DE 1 253 716 11/1967

(Continued)

OTHER PUBLICATIONS

Ullmann's Encyclopedia of Industrial Chemistry, 5. Ed., vol. A5, 1986.

(Continued)

*Primary Examiner*—Virginia Manoharan
(74) *Attorney, Agent, or Firm*—Connolly Bove Lodge & Hutz LLP

(57) ABSTRACT

The disclosure relates to a process for purifying crude caprolactam. The process involves converting a first mixture of 6-amino capronitrile and water to a second mixture of caprolactam ammonia, water, high boilers and low boilers using a catalyst. The ammonia is removed from the second mixture to obtain a third mixture. Water is removed from the third mixture to give crude caprolactam, high boiler and low boilers. Purified caprolactam is then obtained by a series of distillation steps.

16 Claims, 2 Drawing Sheets

U.S. PATENT DOCUMENTS

| | | | |
|---|---|---|---|
| 5,495,016 A | | 2/1996 | Achhammer et al. |
| 5,693,793 A | | 12/1997 | Ritz et al. |
| 5,700,358 A | * | 12/1997 | Fuchs et al. .................... 203/31 |
| 6,635,151 B1 | * | 10/2003 | Bocquenet et al. ............. 203/14 |
| 2003/0114664 A1 | | 6/2003 | Ohlbach et al. |
| 2003/0125546 A1 | | 7/2003 | Bassler et al. |
| 2003/0132098 A1 | | 7/2003 | Luyken et al. |
| 2004/0014965 A1 | | 1/2004 | Amoros et al. |

FOREIGN PATENT DOCUMENTS

| | | |
|---|---|---|
| DE | 100 21 192 A1 | 11/2001 |
| DE | 100 21 199 A1 | 11/2001 |
| EP | 0 411 455 A1 | 2/1991 |
| WO | WO-96/20923 A1 | 7/1996 |
| WO | WO-97/02228 A1 | 1/1997 |
| WO | WO-97/06126 A1 | 2/1997 |
| WO | WO-98/37063 A1 | 8/1998 |
| WO | WO-99/48867 A1 | 9/1999 |
| WO | WO-99/65873 A1 | 12/1999 |
| WO | WO-03/045911 A1 | 6/2003 |

OTHER PUBLICATIONS

Kirk-Othmer, Encyclopedia of Chemical Technology, 4. Ed., vol. 4, 1992.

* cited by examiner

METHOD FOR PURIFYING CAPROLACTAM

This application is a National Stage of PCT/EP2003/12558 filed Nov. 11, 2003 which in turn claims priority from German Application 102 53 094.7 filed Nov. 13, 2002.

The present invention relates to a process for purifying crude caprolactam which has been obtained by
1) converting a mixture (I) comprising 6-aminocapronitrile and water to a mixture (II) comprising caprolactam, ammonia, water, high boilers and low boilers in the presence of a catalyst, then
2) removing ammonia from mixture (II) to obtain a mixture (III) comprising caprolactam, water, high boilers and low boilers, then
3) completely or partly removing water from mixture (III) to obtain crude caprolactam (IV) comprising caprolactam, high boilers and low boilers,
which comprises
   a) feeding the crude caprolactam and an inorganic acid which has a boiling point above the boiling point of caprolactam under the distillation conditions of the following steps b) to h) to a first distillation apparatus C1,
   b) distilling the crude caprolactam and the inorganic acid in the first distillation apparatus C1, and removing a first substream in the bottom region and a second substream in the top region of the distillation apparatus C1.
   c) feeding the second substream from step b) to a second distillation apparatus C2,
   d) distilling the second substream from step b) in the second distillation apparatus C2, and removing a first substream in the bottom region and a second substream in the top region of the distillation apparatus C2,
   e) feeding the first substream from step d) to a third distillation apparatus C3,
   f) distilling the first substream from d) in the third distillation apparatus C3, and removing a first substream in the bottom region and purified caprolactam in the top region of distillation apparatus C3, and
   g) feeding the first substream from step f) to the first distillation apparatus C1.

Processes for preparing caprolactam are common knowledge.

It is likewise common knowledge, for example from Ullmann's Encyclopedia of Industrial Chemistry, 5th Ed., Vol. A5, VCH Verlagsgesellschaft mbH, Weinheim (Germany), 1986, page 46-48, or Kirk-Othmer, Encyclopedia of Chemical Technology, 4th Ed., Vol. 4, John Wiley & Sons, New York, 1992, page 836, that caprolactam which is used for the preparation of polymers has to have a purity of from 99.9 to 99.94%, and the main impurity is typically water in an amount of from 0.04 to 0.1%. Other impurities may be present only in the region of a maximum of a few ppm. For instance, caprolactam can be prepared by Beckmann rearrangement of cyclohexanone oxime with sulfuric acid or oleum. After neutralization of the mixture obtained in this way with ammonia, the caprolactam can be obtained from the ammonium sulfate formed as a by-product by extraction with an organic solvent.

Depending on the processes for preparing the reactants used to synthesize cyclohexanone oxime, such as cyclohexanone and hydroxylammonium sulfate, the oximation and rearrangement conditions, the crude caprolactam which has been obtained by Beckmann rearrangement comprises impurities which differ in their type and amount. Typical impurities of crude caprolactam which has been obtained by Beckmann rearrangement are C-methylcaprolactams, 6-methylvalerolactam and n-pentylacetamide.

For the purification of the crude caprolactam obtained in the Beckmann rearrangement, various processes have been described.

According to DE-A-1253716, the crude caprolactam can be purified by hydrogenation in suspension in the presence of a catalyst and with the addition of an acid.

According to DE-A-1253716, the crude caprolactam can be purified by hydrogenation in suspension in the presence of a catalyst and with the addition of a base.

DD-A-75083 describes a process for purifying crude caprolactam by initially distilling crude caprolactam and subsequently, dissolved in an organic solvent, hydrogenating in the presence of a catalyst and then treating with an ion exchanger.

According to EP-A-411455, the characteristic important quality features for caprolactam can be maintained by continuously hydrogenating the crude caprolactam in a liquid phase process.

Crude caprolactam which is obtained by hydroformylating 3-pentenoic acid and/or its esters to 5-formylvaleric acid/esters as the main products and 4- and 3-formylvaleric acid/esters as the by-products, extractive (WO 97/02228) or distillative (WO 97/06126) removal of these branched formylvaleric acid/esters, aminating hydrogenation of 5-formylvaleric acid/esters to 6-aminocaproic acid/esters and/or 6-aminocapronamide and cyclization of 6-aminocaproic acid/esters or 6-aminocapronamide contains other typical impurities.

For example, the crystallization of crude caprolactam with the addition of 10% by weight of water obtained starting from 5-formylvaleric esters is disclosed by WO 99/48867, Example 1, and starting from mixtures of 6-aminocaproic acid, 6-aminocapronamide and corresponding oligomers by WO 98/37063, Example 9. In this crude caprolactam from which high and low boilers have not been removed before crystallization, 6345 ppm of N-methylcaprolactam, 100 ppm of 5-methylvalerolactam, 78 ppm of valeramide and other impurities were present. The crude caprolactam/water melt was homogenized at 50° C. and then cooled to 30° C. The precipitated crystals were filtered off and washed 2 to 3 times with aqueous caprolactam. 5-Methylvalerolactam and valeramide were depleted to 1 ppm, and N-methylcaprolactam to 51 ppm. 73.6 g of crude lactam provided 33.7 g of pure lactam (caprolactam yield: 45.8%). The specification for the volatile bases (VB) was only attained by a second crystallization. When high and low boilers were removed from the crude caprolactam before the crystallization according to WO 99/48867, Example 3, the caprolactam yield after crystallization was 52%.

WO 99/65873 further discloses the selective adsorption of caprolactam from mixtures with 4-ethyl-2-pyrrolidone, 5-methyl-2-piperidone, 3-ethyl-2-pyrrolidone and 3-methyl-2-piperidone or octahydrophenazine on adsorbents such as activated carbon, molecular sieves or zeolites to obtain pure caprolactam after desorption. This caprolactam removal may be followed by a melt crystallization or a crystallization from a solvent.

It is also known that crude caprolactam can be purified by crystallization, starting from 6-aminocapronitrile according to WO 98/37063, claim 8, and initially hydrolyzing with water to give 6-aminocaproic acid. Water and ammonia formed by hydrolysis are then removed, the 6-aminocaproic acid formed is cyclized and the resulting crude caprolactam is crystallized according to WO 99/48867.

Caprolactam can also be obtained by reacting 6-aminocapronitrile (ACN) with water in the liquid phase in the presence or absence of a catalyst with the release of ammonia.

In addition to caprolactam, water, ammonia and in some cases further liquid diluent, the mixture obtained in this reaction comprises impurities having a boiling point above that of caprolactam (high boilers) and those having a boiling point below that of caprolactam (low boilers).

The example of U.S. Pat. No. 496,941 discloses that crude caprolactam is obtained in a purity of 99.5% after the removal of water, solvent, ammonia, low boilers and high boilers from a mixture obtained in the reaction of ACN with water and solvent.

For crude caprolactam which has been obtained from ACN in the liquid phase, other purification processes are described, since the impurities of such crude caprolactam differ significantly from those of crude caprolactam which has been obtained by other processes, as described in U.S. Pat. No. 5,496,941.

According to U.S. Pat. No. 5,496,941, ACN is converted in a first step in the liquid phase to caprolactam, low boilers, water, ammonia and optionally further solvents are removed simultaneously, high boilers are removed to obtain crude caprolactam in a purity of 99.5%, this crude caprolactam is hydrogenated in the presence of a catalyst, the resulting product is treated with an acidic ion exchanger or sulfuric acid and the resulting product is distilled in the presence of a base.

WO 96/20923 discloses a process for purifying crude caprolactam which stems from liquid phase cyclization of 6-aminocapronitrile with water in the presence of a solvent and of heterogeneous catalysts. In this process, crude caprolactam is initially hydrogenated, then treated with acidic agents and finally distilled in the presence of alkali.

A disadvantage of these two purification processes is that three separate reaction steps are required for the preparation of pure caprolactam.

DE 100 21 199 A1 and DE 100 21 192 disclose the purification by crystallization of caprolactam obtained by liquid or gas phase cyclization after removal of ammonia and water.

Figure 1:
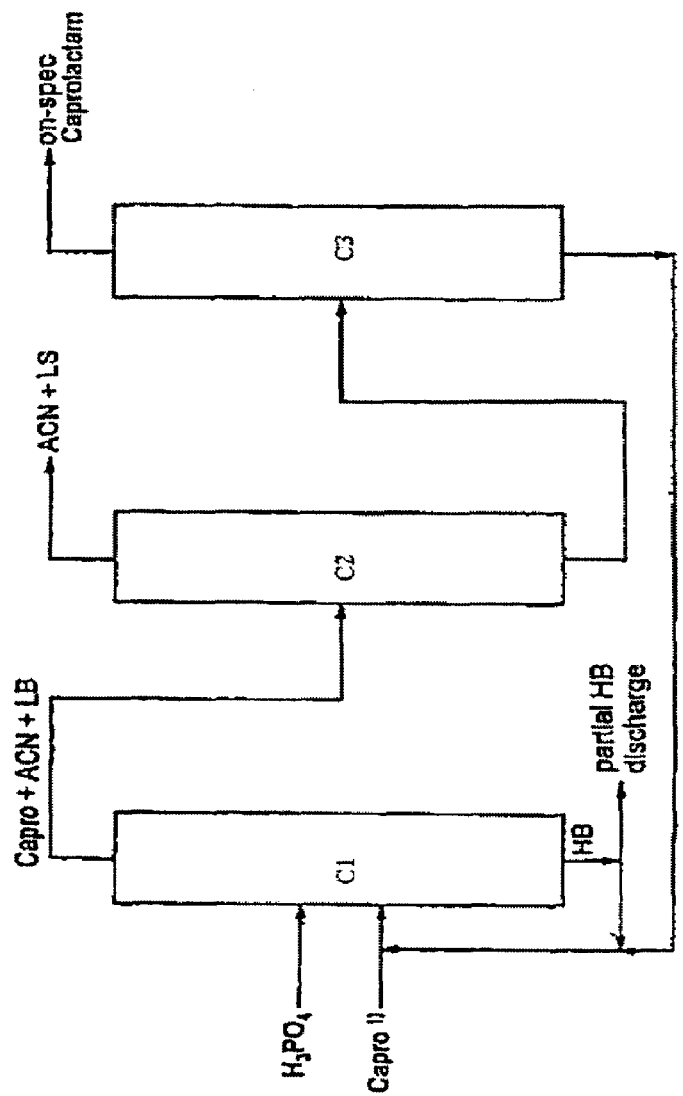
FIG. 1 illustrates an embodiment of the disclosed process involving the distillation of crude caprolactam to form purified caprolactam.
Figure 2:
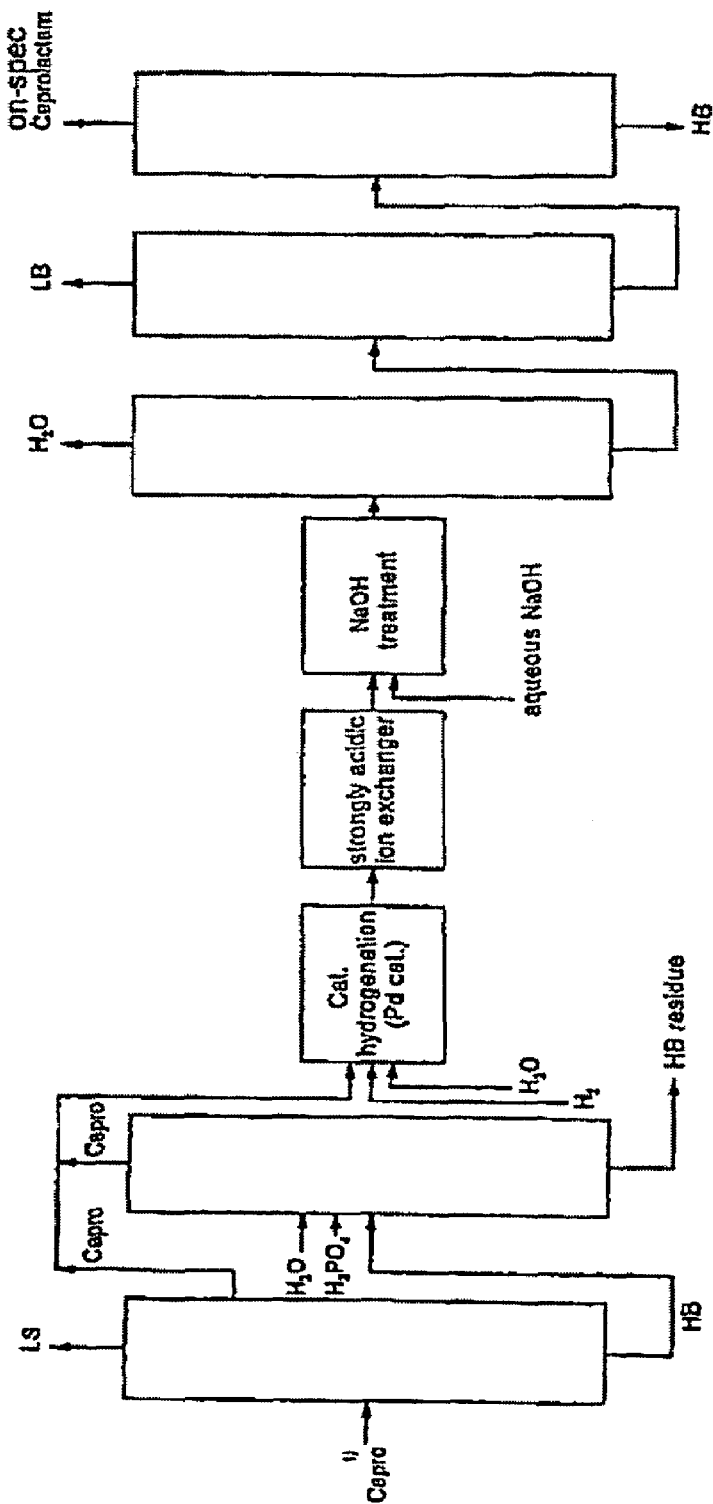
FIG. 2 illustrates an embodiment of the disclosed process with a cyclization effluent from which $NH_3$, $C_2H_5OH$ and $H_2O$ have been removed.

The processes mentioned for purifying crude caprolactam which has been obtained from ACN have the disadvantage that they are technically complicated and energy-intensive, in particular as a consequence of the numerous separating steps.

It is an object of the present invention to provide a process which enables the preparation of caprolactam which has been obtained starting from ACN, in high purity and in a technically simple and energy-saving manner.

We have found that this object is achieved by the process defined at the outset.

In the process according to the invention, crude caprolactam is used which has been obtained by reacting 6-aminocapronitrile with water according to steps 1), 2) and 3).

In step 1), a mixture (I) comprising 6-aminocapronitrile, water and optionally liquid diluent is converted to a mixture (II) comprising caprolactam, ammonia, water, optionally liquid diluent, high boilers and low boilers in the presence of a solid which catalytically supports the conversion.

The ACN required for step 1) can, as generally known from Ullmann's Encyclopedia of Industrial Chemistry, 5th Ed., Vol. A5, VCH Verlagsgesellschaft mbH, Weinheim (Germany), 1986, page 46, FIG. 8, be obtained from adiponitrile.

Particular useful processes are the partial catalyzed hydrogenation of adiponitrile in the presence of ammonia as a solvent and, for example as a suspension catalyst, rhodium on magnesium oxide (U.S. Pat. No. 4,601,859), Raney nickel (U.S. Pat. No. 2,762,835, WO 92/21650), nickel on aluminum oxide (U.S. Pat. No. 2,208,598), or, as a fixed bed catalyst, Cu—Co—Zn spinel (DE-B-954416, U.S. Pat. No. 2,257,814) or iron (DE-A-42 35 466) or a process according to U.S. Pat. No. 2,245,129, U.S. Pat. No. 2,301,964, EP-A-150295 or a process described in U.S. Pat. No. 5,496,941.

The adiponitrile required for this conversion is prepared industrially, for example, by double hydrocyanation of butadiene in the presence of nickel-containing catalysts and is commercially available, for example, from Aldrich-Chemie Gesellschaft mbH & Co. KG, Steinheim, Germany.

According to U.S. Pat. No. 4,628,085, mixture (I) can be converted to mixture (II) in the gas phase over silica gel at 300° C.

Equally, this conversion can be carried out according to U.S. Pat. No. 4,625,023 in the gas phase over a silica gel or copper/chromium/barium-titanium oxide catalyst.

Mixture (I) can also be converted to mixture (II), for example, according to EP-A-659 741, WO 96/22974, DE 19632006, WO 99/47500 or WO 99/28296.

The conversion can preferably be carried out in the gas phase at temperatures of generally from 200 to 550° C., preferably from 250 to 400° C.; the pressure is generally in the range from 0.01 to 10 bar, preferably at atmospheric pressure, although care has to be taken that the reaction mixture is predominantly gaseous under the conditions employed.

The catalyst hourly space velocities are typically from 0.05 to 2 kg, preferably from 0.1 to 1.5 kg, in particular from 0.2 to 1 kg, of 6-aminocapronitrile per liter of catalyst volume per hour.

The conversion may be carried out batchwise, but preferably continuously.

Useful reactors are advantageously those as generally known for gas phase reactions over moving or stationary solid catalysts. Preference is given to using a fluidized bed reactor, preferably fixed bed reactor, such as a tray reactor, in particular a tubular reactor. Combinations of such reactors are also possible.

Generally from 1 to 50 mol, preferably from 1 to 10 mol, of water are used per mole of ACN.

The mixture (I) may also comprise further organic compounds which are in gaseous form under the reaction conditions, such as alcohols, amines or aromatic or aliphatic hydrocarbons.

Useful catalytically active compounds of the catalysts are, for example, silicon dioxide as pyrogenic silicon dioxide, as silica gel, kieselguhr, quartz or mixtures thereof, copper chromite, preferably aluminum oxide, titanium oxide, preferably titanium dioxide, lanthanum phosphates, lanthanum oxides, and also mixtures of such compounds.

Aluminum oxide is suitable in all modifications which can be obtained by heating the precursor compounds aluminum hydroxide (gibbsite, boehmite, pseudoboehmite, bayerite and diaspor) at different temperatures. These include in particular gamma- and alpha-aluminum oxide and their mixtures.

Titanium dioxide is amorphous and suitable in all its modifications, preferably anatase and rutile, and also mixtures of such modifications.

Lanthanum phosphates are suitable in their various modifications, stoichiometric ratios between lanthanum and phosphate units and degrees of condensation of the phosphate units (monophosphate, oligophosphates such as diphosphates or triphosphates, polyphosphates), individually or in a mixture.

These compounds can be used in the form of powders, meal, spall, extrudates or pressed to tablets. The form of the compounds is generally determined by the requirements of the particular reaction method, and powder or meal are advantageously used in the fluidized bed method. In the fixed bed method, tablets or extrudates having diameters of between 1 mm and 6 mm are customarily used.

The compounds can be used in pure form (content of the particular compounds >80% by weight), as a mixture of the abovementioned compounds, in which case the sum of the abovementioned compounds should be >80% by weight, or as a supported catalyst, in which case the abovementioned compounds can be applied to a mechanically and chemically stable support, usually having a high surface area.

The pure compounds may have been prepared by precipitating from aqueous solutions, for example titanium dioxide by the sulfate process or by other processes such as pyrogenic preparation of fine aluminum oxide, titanium dioxide or zirconium dioxide powders, which are commercially available.

Several methods are available for preparing the mixtures of various compounds. The compounds or their precursor compounds which can be converted to the oxides by calcining can be prepared, for example, by coprecipitation from solution. This generally results in very good distribution of the two compounds used being obtained. The compound or precursor mixtures can also be precipitated by precipitating one compound or precursor in the presence of finely divided particles of the second compound or precursor present as a suspension. A further method consists in mechanical mixing of the compound or precursor powder, and this mixture may find use as a starting material for producing extrudates or tablets.

All methods described in the literature are in principle suitable for preparing supported catalysts. For instance, the compounds can be applied to the support in the form of their sols by simple impregnation. Drying and calcining customarily remove the volatile constituents of the sol from the catalyst. Such sols are commercially available for titanium dioxide and aluminum oxide.

A further means of applying layers of the catalytically active compounds is to hydrolyze or pyrolyze organic or inorganic compounds. For instance, a ceramic support can be covered with a thin layer of titanium dioxide by hydrolysis of titanium isopropoxide or other titanium alkoxides. Further suitable compounds include $TiCl_4$ and aluminum nitrate. Suitable supports are powders, extrudates or tablets of the compounds mentioned themselves or other stable compounds such as steatite or silicon carbide. The supports used may be macroporous to improve the mass transfer.

The reaction can be carried out in the presence of a gas inert with regard to the conversion of mixture (I) to mixture (II), preferably argon, in particular nitrogen. The volume ratio of inert gas to the ACN which is gaseous under the reaction conditions may advantageously be up to 100.

Particular preference is given to step 1) being a process as described in U.S. Pat. No. 5,646,277 or U.S. Pat No. 5,739,324 or FR-A-2029540.

According to FR-A-2029540, the reaction can be carried out in the presence of catalysts which are metallic Zn or Cu powder or oxides, hydroxides, halides, cyanides of rubidium, lead, mercury or of the elements having an atomic number of from 21 to 30 or from 39 to 48. The catalysts described are used as suspension catalysts in batchwise stirred autoclaves.

In these processes, the reaction is carried out in the liquid phase at temperatures of generally from 140 to 320° C., preferably from 160 to 280° C.; the pressure is generally in the range from 1 to 250 bar, preferably from 5 to 150 bar, although care has to be taken that the reaction mixture is predominantly liquid under the conditions employed. The residence times are generally in the range from 1 to 120 min, preferably from 1 to 90 min and in particular from 1 to 60 min. In some cases, residence times of from 1 to 10 min have proven entirely sufficient.

The conversion can be carried out batchwise, but preferably continuously. Useful reactors include a stirred tank, autoclave, preferably a fixed bed tubular reactor. Combinations of such reactors are also possible.

Generally at least 0.1 mol, preferably from 0.5 to 100 mol and in particular from 1 to 20 mol, of water are used per mole of ACN.

Advantageously, the ACN is used in the form of a from 1 to 50% by weight, in particular from 5 to 50% by weight, more preferably from 5 to 30% by weight, solution in water, in which case the solvent is then at the same time a reaction partner, or in mixtures comprising water and a liquid diluent. Examples of useful diluents include alkanols, such as methanol, ethanol, n- and i-propanol, n-, i- and t-butanol, and polyols such as diethylene glycol and tetraethylene glycol, hydrocarbons such as petroleum ether, benzene, toluene, xylene, lactams such as pyrrolidone or caprolactam or alkyl-substituted lactams such as N-methylpyrrolidone, N-methylcaprolactam or N-ethylcaprolactam and also carboxylic esters, preferably of carboxylic acids having from 1 to 8 carbon atoms. Ammonia may also be present in the reaction. It will be appreciated that mixtures of organic liquid diluents may also find use. Mixtures of water and alkanols in a water/alkanol weight ratio of 1-75/25-99, preferably 1-50/50-99 have in some cases proven particularly advantageous.

It is in principle also possible to employ ACN as a reactant and at the same time to employ solvents.

Useful heterogeneous catalysts are, for example: acids, basic or amphoteric oxides of the elements of the second, third or fourth main group of the Periodic Table, such as calcium oxide, magnesium oxide, boron oxide, aluminum oxide, tin oxide or silicon dioxide as pyrogenic silica, as silica gel, kieselguhr, quartz or mixtures thereof, and also oxides of metals of the second to sixth transition group of the Periodic Table, such as amorphous titanium oxide, as anatase or rutile, zirconium oxide, zinc oxide, manganese oxide or mixtures thereof. It is likewise possible to use oxides of lanthanides and actinides, such as cerium oxide, thorium oxide, praseodymium oxide, samarium oxide, rare earth mixed oxides, or mixtures thereof with the aforementioned oxides. Further catalysts may, for example, be: vanadium oxide, niobium oxide, iron oxide, chromium oxide, molybdenum oxide, tungsten oxide or mixtures thereof. Mixtures of the oxides mentioned with each other are likewise possible. Some sulfides, selenides and tellurides, such as zinc telluride, zinc selenide, molybdenum sulfide, tungsten sulfide, sulfides of nickel, zinc and chromium, can also be used.

The aforementioned compounds may be doped with compounds of the 1st and 7th main group of the Periodic Table or contain them.

Further suitable catalysts include zeolites, phosphates and heteropolyacids, and also acidic and alkaline ion exchangers, for example Nafion.

These catalysts may optionally each comprise up to 50% by weight of copper, tin, zinc, manganese, iron, cobalt, nickel, ruthenium, palladium, platinum, silver or rhodium.

Particularly preferred catalysts which have very high yields, conversions, selectivities and on-stream times under the above-described reaction conditions are heterogeneous catalysts based on titanium oxide, zirconium oxide, cerium oxide and aluminum oxide. These may be used in the form of powders, meal, spall, extrudates or pressed to tablets. The form of the oxides is generally determined by the requirements of the particular reaction method, and powder or meal are used in suspension. In the fixed bed method, it is customary to use tablets or extrudates having diameters between 1 mm and 10 mm.

Aluminum oxide is suitable in all modifications which can be obtained by heating the precursor compounds aluminum hydroxide (gibbsite, boehmite, pseudoboehmite, bayerite and diaspore) at different temperatures. These include in particular gamma- and alpha-aluminum oxide and their mixtures.

The oxides can be used in pure form (content of the particular oxide >80% by weight), as a mixture of the abovementioned oxides, in which case the sum of the abovementioned oxides should be >80% by weight, or as a supported catalyst, in which case the abovementioned oxides can be applied to a mechanically and chemically stable support, usually having a high surface area.

The pure oxides may have been prepared by precipitating from aqueous solutions, for example titanium dioxide by the sulfate process or by other processes such as pyrogenic preparation of fine aluminum oxide, titanium dioxide or zirconium dioxide powders, which are commercially available.

Several methods are available for preparing the mixtures of various oxides. The oxides or their precursor compounds which can be converted to the oxides by calcining can be prepared, for example, by coprecipitation from solution. This generally results in very good distribution of the two oxides used being obtained. The oxide or precursor mixtures can also be precipitated by precipitating one oxide or precursor in the presence of finely divided particles of the second oxide or precursor present as a suspension. A further method consists in mechanical mixing of the oxide or precursor powder, and this mixture may find use as a starting material for producing extrudates or tablets.

All methods described in the literature are in principle suitable for preparing supported catalysts. For instance, the oxides can be applied to the support in the form of their sols by simple impregnation. Drying and calcining customarily remove the volatile constituents of the sol from the catalyst. Such sols are commercially available for titanium dioxide, aluminum oxide and zirconium dioxide.

A further possibility for applying layers of the active oxides is to hydrolyze or pyrolyze organic or inorganic oxides. For instance, a ceramic support can be covered with a thin layer of titanium dioxide by hydrolysis of titanium isopropoxide or other titanium alkoxides. Further suitable compounds include $TiCl_4$, zirconyl chloride aluminum nitrate and cerium nitrate. Suitable supports are powders, extrudates or tablets of the oxides mentioned themselves or other stable oxides such as silicon dioxide. The supports used may be macroporous to improve the mass transfer.

In step 2), ammonia is removed from mixture (II) to obtain a mixture (III) comprising caprolactam, water, any liquid diluent, high boilers and low boilers.

The ammonia can in principle be removed from mixture (II) by processes known per se for separation of materials, such as extraction or preferably distillation, or a combination of such processes.

The distillation may advantageously be carried out at bottom temperatures of from 60 to 220° C., in particular from 100 to 220° C. It is customary to set a pressure, measured at the top of the distillation apparatus, of from 2 to 30 bar absolute.

Useful apparatus for the distillation is apparatus customary for this purpose, as described, for example, in Kirk-Othmer, Encyclopedia of Chemical Technology, 3rd Ed., Vol. 7, John Wiley & Sons, New York, 1979, page 870-881, such as sieve tray columns, bubble-cap tray columns, and columns having structured packing or random packing.

The distillation can be carried out in a plurality of, such as 2 or 3, columns, advantageously a single column.

In step 3), water, fully or partly, and any liquid diluent are removed from mixture (III) to obtain crude caprolactam (IV) comprising caprolactam, high boilers and low boilers.

When a liquid diluent has been used in step 1), water and liquid diluent can be removed in step 3) simultaneously, or the water can be removed before or after the liquid diluent.

The water and any liquid diluent from mixture (III) can in principle be removed by processes known per se for separation of materials, such as extraction, crystallization or preferably distillation, or a combination of such processes.

The distillation may advantageously be carried out at bottom temperatures of from 50 to 250° C., in particular from 100 to 230° C.

Useful apparatus for the distillation is apparatus customary for this purpose, as described, for example, in Kirk-Othmer, Encyclopedia of Chemical Technology, 3rd Ed., Vol. 7, John Wiley & Sons, New York, 1979, page 870-881, such as sieve tray columns, bubble-cap tray columns, and columns having structured packing or random packing.

Particular preference is given to heat-integrated, multistage removal of the water and of any liquid diluent.

Before feeding the crude caprolactam (IV) into step a), it is possible to remove low boilers or high boilers, advantageous to remove only the high boilers, also advantageous to remove only the low boilers, particularly advantageous to remove neither low boilers nor high boilers, especially to remove the low boilers and the high boilers, from the crude caprolactam (IV). When low boilers and high boilers are removed from the crude caprolactam, the low boilers can be removed before, after or together with, more preferably before, the high boilers.

In the case of removal of the low boilers and high boilers or only high boilers or only low boilers, the removal can in principle be effected by processes known per se for separation of materials, such as extraction, crystallization or preferably distillation, or a combination of such processes.

The distillation may advantageously be carried out at bottom temperatures of from 50 to 250° C., in particular from 100 to 230° C. It is customary to set a pressure, measured at the top of the distillation apparatus, of from 1 to 500 mbar absolute, preferably from 5 to 100 mbar absolute.

Useful apparatus for the distillation is apparatus customary for this purpose, as described, for example, in Kirk-Othmer, Encyclopedia of Chemical Technology, 3rd Ed., Vol. 7, John Wiley & Sons, New York, 1979, page 870-881, such as sieve tray columns, bubble-cap tray columns, and columns having structured packing or random packing.

The distillation for removing the low boilers can be carried out in a plurality of, such as 2 or 3, columns, advantageously a single column.

The distillation for removing the high boilers can be carried out in a plurality of, such as 2 or 3, columns, advantageously a single column.

The low boilers in this removal are in particular 6-aminocapronitrile.

According to the invention, the crude caprolactam which preferably stems from the tops of the high boiler removal or from the bottoms of the low boiler removal and an inorganic acid which has a boiling point above the boiling point of caprolactam under the distillation conditions of subsequent steps b) to g) are fed to step a) of a first distillation apparatus C1.

Useful inorganic acids which have a boiling point above the boiling point of caprolactam under the distillation conditions of subsequent steps b) to g) are, for example, sulfuric acid, phosphoric acid, boric acid, or their acidic salts, such as alkali metal, earth metal or alkaline earth metal salts, or mixtures of such acids and salts, preferably the acids or their mixtures.

In an advantageous embodiment, phosphoric acid or its acidic salts, such as alkali metal, earth metal or alkaline earth metal salts or their mixtures, in particular phosphoric acid, can be used. These acids or acidic salts can be used in pure form or in a mixture with a liquid diluent, such as water.

Crude caprolactam and inorganic acid can be fed separately to the first distillation apparatus C1 or preferably mixed before being fed to the first distillation apparatus C1 and fed to this distillation apparatus as a mixture.

The amount of inorganic acid may advantageously be set in such a way that the content of free acid, which can be determined by titration, in the bottom region of the first distillation apparatus C1 is in the range from 0.1 to 5% by weight, in particular from 0.5 to 3% by weight, based on the overall mixture present in this bottom region.

Useful apparatus for the first distillation apparatus includes apparatus customary for this purpose, as described, for example, in Kirk-Othmer, Encyclopedia of Chemical Technology, 3rd Ed., Vol. 7, John Wiley & Sons, New York, 1979, page 870-881, such as sieve tray columns, bubble-cap tray columns, and columns having structured packing or random packing.

The distillation can be carried out in a plurality of, such as 2 or 3, columns, advantageously a single column.

When the distillation apparatus used is a column, this column may advantageously have from 1 to 30 theoretical plates, in particular from 5 to 20 theoretical plates.

In a preferred embodiment, crude caprolactam (IV) can be introduced to the top of the distillation apparatus C1.

In step b), the crude caprolactam and the inorganic acid are distilled in the first distillation apparatus C1.

For this distillation, bottom temperatures of at least 120° C., in particular at least 140° C., have proven advantageous.

For this distillation, bottom temperatures of at most 220° C., preferably at most 200° C., in particular at most 190° C. have proven advantageous.

Furthermore, the preferred pressure at the top of the first distillation apparatus C1 is at least 10 mbar, in particular at least 40 mbar.

Futhermore, the preferred pressure at the top of the first distillation apparatus C1 is at most 120 mbar, in particular at most 100 mbar.

In this distillation, a first substream in the bottom region and a second substream in the top region are removed from the distillation apparatus C1.

The optimum size of the two substreams for the performance of the process according to the invention can be determined by a few simple preliminary experiments.

Advantageously, a portion of the first substream from step b) can be mixed in step a) with the crude caprolactam.

The optimum size of the proportion of this first substream mixed with the crude caprolactam for the performance of the process according to the invention may be determined by a few simple preliminary experiments.

According to observations made hitherto, a weight ratio of said proportion of the substream to crude caprolactam of at least 0.01 has proven advantageous; moreover, a weight ratio of said proportion of the substream to crude caprolactam of at most 0.3 has proven advantageous.

In step c), the second substream from step b) is fed to a second distillation apparatus C2. Useful apparatus for the second distillation apparatus includes apparatus customary for this purpose, as described, for example, in Kirk-Othmer, Encyclopedia of Chemical Technology, 3rd Ed., Vol. 7, John Wiley & Sons, New York, 1979, page 870-881, such as sieve tray columns, bubble-cap tray columns, and columns having structured packing or random packing.

The distillation can be carried out in a plurality of, such as 2 or 3, columns, advantageously a single column. When the second distillation apparatus used is a column, this column may advantageously have from 3 to 30 theoretical plates, in particular from 5 to 20 theoretical plates.

In step d), the second substream from step b) is distilled in the second distillation apparatus C2.

According to observations made hitherto, bottom temperature and pressure can be selected within a wide range, although a bottom temperature of about 200° C. and a bottom temperature of about 190° C. are advantageous.

In this distillation, a first substream in the bottom region and a second substream in the top region are removed from the distillation apparatus C2.

The optimum size of the two substreams for the performance of the process according to the invention can be easily determined by a few simple preliminary experiments.

In an advantageous embodiment, the second substream from step d) can be recycled completely or partly, preferably completely between step 3) and step a), especially in the event of removal of the low boilers between these two steps, before the removal of the low boilers.

In step e), the first substream from step e) is fed to a third distillation apparatus C3.

Useful apparatus for the third distillation apparatus includes apparatus customary for this purpose, as described, for example, in Kirk-Othmer, Encyclopedia of Chemical Technology, 3rd Ed., Vol. 7, John Wiley & Sons, New York, 1979, page 870-881, such as sieve tray columns, bubble-cap tray columns, and columns having structured packing or random packing.

The distillation can be carried out in a plurality of, such as 2 or 3, columns, advantageously a single column.

When the third distillation apparatus used is a column, this column may advantageously have from 3 to 30 theoretical plates, in particular from 5 to 20 theoretical plates.

In step f), the second substream from step d) is distilled in the third distillation apparatus C3.

According to observations made hitherto, bottom temperature and pressure in this distillation may be selected within a wide range, although a bottom temperature of about 200° C. and a bottom temperature of about 190° C. are advantageous.

In this distillation, a first substream in the bottom region and purified caprolactam in the form of a second substream in the top region are removed from the distillation apparatus C3.

The optimum size of the two substreams for the performance of the process according to the invention can easily be determined by a few simple preliminary experiments.

According to observations made hitherto, a weight ratio of the substream removed in the top region to the substream removed in the bottom region of at least 0.3 has proven advantageous; moreover, a weight ratio of the substream removed in the top region to the substream removed in the bottom region of at most 2.0 has proved advantageous.

According to the invention, in step g), the first substream from step f) is completely or partly, preferably completely, fed to the first distillation apparatus C1. In an advantageous embodiment, this stream can be introduced to the top of the distillation apparatus C1.

In a particularly preferred embodiment, the pressure in one, two or three of the distillation apparatus C1, C2, C3 may be at least 40 mbar, in particular at least 100 mbar.

It was surprising that the invention succeeds in distillatively converting crude caprolactam, merely with the addition of mineral acids, to caprolactam which has the high purity required in accordance with the specification for fiber production. According to U.S. Pat. No. 5,496,941, this requires catalytic hydrogenation under pressure, treatment with acids and treatment with bases.

EXAMPLE

Low boilers were initially removed from a crude caprolactam stream down to a residual content of less than 3 ppm of ACN. Subsequently, high boilers were removed and the caprolactam obtained overhead.

85 kg/h of the low and high boiler-free crude caprolactam were passed from a vessel V1 to the top region of a column C1.

Column C1 was operated at a top pressure of 50 mbar and a bottom temperature of 170° C.

5.2 kg/h were removed via the bottom of column C1, of which 0.2 kg/h were discharged and 5.0 kg/h recycled into vessel V1.

Sufficient aqueous $H_3PO_4$ was metered into the bottom of column C1 that the content of free acid was 1%.

The top takeoff of column C1 was passed into a second column C2.

Column C2 was operated at a top pressure of 50 mbar.

5.0 kg/h were removed via the top of column C2 and fed to workup in which the crude caprolactam was obtained.

The bottom takeoff from column C2 was passed into the bottom region of a column C3. Column C3 was operated at a top pressure of 50 mbar.

100 kg/h were removed via the bottom and recycled into the top region of column C1.

79.75 kg/h of pure caprolactam were removed overhead.

The properties of the in pure caprolactam were determined as follows:

| Property | Analytical method | Measurement | Specification |
|---|---|---|---|
| E290 | ISO 7059 | 0.024 | <0.05 |
| Color number | ISO 8112 | 0.36 | <5 |
| Permanganate index | ISO 8660 | 2.51 | <4 |
| Free acids | acidimetric titration of an aqueous caprolactam solution against Tashiro indicator | 0.024 meq/kg | <0.05 meq/kg |
| Volatile bases | ISO 8661 | 0.252 meq/kg | <0.4 meq/kg |

The specification relates to commercially available caprolactam.

We claim:

1. A process for purifying crude caprolactam comprising
    1) converting a mixture (I) comprising 6-aminocapronitrile and water to a mixture (II) comprising caprolactam, ammonia, water, high boilers and low boilers in the presence of a catalyst,
    2) removing ammonia from the mixture (II) to obtain a mixture (III) comprising caprolactam, water, high boilers and low boilers,
    3) completely or partly removing water from the mixture (III) to obtain crude caprolactam (IV) comprising caprolactam, high boilers and low boilers, and
    4) distilling the crude caprolactam (IV) comprising
        a) feeding the crude caprolactam (IV) and an inorganic acid which has a boiling point above the boiling point of caprolactam to a first distillation apparatus C1,
        b) distilling the crude caprolactam IV and the inorganic acid in the first distillation apparatus C1, and removing a first substream in the bottom region and a second substream in the top region of the distillation apparatus C1,
        c) feeding the second substream from step b) to a second distillation apparatus C2,
        d) distilling the second substream from step b) in the second distillation apparatus C2, and removing a first substream in the bottom region and a second substream in the top region of the distillation apparatus C2,
        e) feeding the first substream from step d) to a third distillation apparatus C3,
        f) distilling the first substream from d) in the third distillation apparatus C3, and removing a first substream in the bottom region of distillation apparatus C3 and removing purified caprolactam in the top region of distillation apparatus C3, and
        g) feeding the first substream from step f) to the first distillation apparatus C1.

2. A process as claimed in claim 1, wherein mixture (I) further comprises an organic liquid diluent.

3. A process as claimed in claim 2, wherein the liquid diluent is removed in step 3), before, during or after the removal of water from mixture (III).

4. A process as claimed in claim 1, wherein low boilers are removed or high boilers are removed or low boilers and high boilers are removed between step 3) and step 4 a).

5. A process as claimed in claim 4, wherein first low boilers and then high boilers are removed.

6. A process as claimed in claim 4, wherein 6-aminocapronitrile is removed as a low boiler.

7. A process as claimed in claim 1, wherein the inorganic acid used is phosphoric acid.

8. A process as claimed in claim 1, wherein the weight ratio of the substream comprising purified caprolactam removed in the top region to the substream removed in the bottom region of the distillation apparatus C3 is in the range from 0.3 to 2.0.

9. A process as claimed in claim 8, wherein the inorganic acid used is phosphoric acid.

10. A process as claimed in claim 1, wherein at least a portion of the first substream obtained in step b) is mixed with the crude caprolactam (IV).

11. A process as claimed in claim 10, wherein the weight ratio of the first substream obtained from the distillation apparatus C1 that is mixed with the crude caprolactam (IV) is in the range from 0.01 to 0.3.

12. A process as claimed in claim 11, wherein at least a portion of the second substream obtained from the distillation apparatus C2 is recycled in step 3) before the low boilers are removed.

13. A process as claimed in claim 1, wherein at least a portion of the second substream obtained from the distillation apparatus C2 is recycled in step 3).

14. A process as claimed in claim 1, wherein the bottom temperature in the distillation apparatus C1 is in the range from 120 to 200° C.

15. A process as claimed in claim 1, wherein the pressure in one, two or three of distillation apparatus C1, C2, C3 is at least 40 bar, measured in the top region 16. A process as claimed in claim 1, wherein the first substream from distillation apparatus C3 is introduced into of the distillation apparatus C1.

\* \* \* \* \*